(12) United States Patent
Sellin et al.

(10) Patent No.: US 8,637,062 B2
(45) Date of Patent: Jan. 28, 2014

(54) COATED IMPLANT

(75) Inventors: Lothar Sellin, Aachen (DE); Bock-Sun Han, Aachen (DE); Annelotte Autschbach, Aachen (DE)

(73) Assignee: Bock-Sun Han (DE)

( * ) Notice: Subject to any disclaimer, the term of this patent is extended or adjusted under 35 U.S.C. 154(b) by 693 days.

(21) Appl. No.: 12/442,188

(22) PCT Filed: Sep. 21, 2007

(86) PCT No.: PCT/EP2007/008246
§ 371 (c)(1),
(2), (4) Date: Oct. 6, 2010

(87) PCT Pub. No.: WO2008/034627
PCT Pub. Date: Mar. 27, 2008

(65) Prior Publication Data
US 2011/0066229 A1    Mar. 17, 2011

(30) Foreign Application Priority Data

Sep. 22, 2006  (DE) .......... 10 2006 045 272
Apr. 2, 2007   (DE) .......... 10 2007 016 151

(51) Int. Cl.
*C07H 21/04* (2006.01)
*A61F 2/00* (2006.01)
*A61F 2/06* (2013.01)
*A61F 2/82* (2013.01)
*A61L 31/16* (2006.01)
*A61L 31/10* (2006.01)
*A61L 31/08* (2006.01)

(52) U.S. Cl.
USPC ....... 424/422; 424/423; 536/24.33; 623/1.41; 623/1.44; 623/1.46

(58) Field of Classification Search
None
See application file for complete search history.

(56) References Cited

U.S. PATENT DOCUMENTS

2003/0229393 A1* 12/2003 Kutryk et al. .............. 623/1.46
2005/0281857 A1* 12/2005 Heyer et al. ................ 424/423
2006/0068416 A1*  3/2006 Schluesener et al. ......... 435/6

OTHER PUBLICATIONS

Witkowski et al., Biochemistry 38(36): 11643-50, Sep. 7, 1999.*

\* cited by examiner

*Primary Examiner* — Phuong Huynh
(74) *Attorney, Agent, or Firm* — Berliner & Associates

(57) ABSTRACT

Implant provided with a coating, with the implant being provided with an amino-functionalized parylene coating, an oligonucleotide and/or an oligopeptide having a specific bonding affinity with CD34-positive cells.

13 Claims, No Drawings

COATED IMPLANT

REFERENCE TO SEQUENCE LISTING

A Sequence Listing is submitted electronically via EFS-Web as an ASCII formatted text file with the name "BSTD0005ST25"; the file was created on Jul. 9, 2013, is 2 kilobytes in size, and is incorporated herein by reference in its entirety.

BACKGROUND

1. Field of the Invention

The invention relates to an implant which is provided with at least one coat. The implant is primarily intended for the vascular system and, in particular, to be used as stent, for example as coronary stent, but may as well be implanted elsewhere.

2. Related Art

Stents are placed into blood vessels with the help of endovascular techniques to permanently eliminate narrow passages or, if thought expedient, close off fistulas or aneurysms. In any case, they are meant to ensure the vessel into which they are placed remains capable of being passed through.

Other implants, especially those used in the coronary area, serve to eliminate defects, for example vascular grafts, bone substitutes, joint substitutes, cardiac valves, closures for the duktus botalli, as well as special implants used to obstruct fistulas and rectify arteriovenous malformations. The invention is described below primarily with reference being made to stents.

Complications frequently arising with stents are linked with the so-called restenosis, i.e. the reclosing of the vessel after a stent has been implanted. Restenosis is due to a proliferation of cells, especially smooth muscle cells, settling on the inner wall of the stent and leading to the recurrent narrowing of the free lumen of the vessel in the area of the stent. In the event of an excessive cell deposition the otherwise desirable ingrowing of the stent may bring about the recurrence of severe vessel narrowing in the stent area which may lead to life-threatening situations, especially if the coronary area is concerned.

One of the reasons restenosis occurs is that when implanting a stent the endothelium is frequently injured causing inflammatory reactions and the liberation of growth factors which in turn results in the proliferation of cells being promoted. Injuries to the vessel wall are mainly due to the stent being firmly pressed against the vessel wall when customary balloon implantation techniques are employed, said pressure not only being exerted with a view of expanding the vessel to achieve an appropriate lumen but also to anchor the stent within the vessel wall in the interest of adequately securing it at the placement site.

Assumptions currently are that restenosis is decisively determined by circumstances arising within the first weeks following implantation. As the wounds in the vessel wall caused by the implanting process heal the inflammatory reactions and liberation of growth factors subside and the proliferation of cells comes to a standstill. Nevertheless, by that time the cell layers accumulated on the inner wall of the stent have formed a basis for new deposits and attachments which may give rise to a long-term restenosis process.

There are two different reasons for restenosis resulting from the placement of stents. On the one hand, this is due to the fact that during the period immediately following implantation the surface of the stent is directly exposed to the blood stream so that an acute thrombosis may occur on account of the foreign surface thus created causing the blood vessel to be obstructed again. On the other hand, there are the implantation-induced vessel wall injuries and the inflammatory processes associated with them. The processes encountered here as well as the liberation of growth factors produce an intensified proliferation of the smooth muscle cells and, even after a short time, cause the relevant vessel to be reclosed due to uncontrollable growth.

After some weeks the stent starts to grow into the tissue of the blood vessel. As a rule, this leads to the stent being entirely embraced by smooth muscle cells so that it is no longer in contact with blood. Although stent ingrowth is actually a desirable process, cicatrization may become too pronounced, however, and not only lead to the stent surface being covered but also causes the entire inner space of the stent to become overgrown (neointimahyperplasia).

In all cases implanted stents remain in the tissue as foreign objects without being integrated there on a permanent basis.

There are a number of approaches aimed at solving the problem of restenosis.

From a mechanical viewpoint the stent is smoothed on all sides by means of a thorough polishing method so as to prevent the deposition of cell material and injuring the endothelium due to roughness and burrs. This method was successful to some degree but so far a certain restenosis rate in the range of 15% could hardly be fallen below.

Unsuccessful attempts have been made to solve the problem of thrombosis-induced restenosis by providing the stent with heparin, refer to J. Whöne et al., European Heart Journal 2001, 22, 1808-1816. Being an anticoagulant heparin exclusively addresses restenosis induced by thrombosis and, moreover, is fully effective only in the form of a solution. In this case a medical treatment has become accepted.

First attempts to prevent neointimal proliferation by coating the stents did not meet with resounding success. So far, neither coatings consisting of gold nor those of silicon carbide or carbon yielded clear and throughout positive results.

It was also attempted to provide stents with proliferation inhibiting medicine to counteract cell proliferation. Known medical agents for this purpose are paclitaxel and rapamycin. Stents provided with these agents currently offer a restenosis rate which is more favorable than that of polished stents. Nevertheless, the restenosis rate needs to be improved in this case as well.

U.S. Pat. No. 5,891,108 discloses a stent of hollow configuration the interior of which contains pharmaceutical agents released through a multitude of openings arranged in the stent. EP-A-1 127 582 describes another variant of a stent of a design suited to accommodate active substances. For example, medical agent-containing stent coatings are known from WO 95/03036 A which in particular describes coatings containing paclitaxel.

Stents finished in this manner are design-wise active agent reservoirs releasing the pharmaceutical active substance locally, at a high concentration and over a relatively long time span.

Whereas stents not finished in a proliferation-inhibiting manner are covered by a protective cell layer within a few months, proliferation-inhibiting medical agents, for example rapamycin and paclitaxel, counteract this healing mechanism. This causes the smooth muscle cells to be no longer able to embrace the stent or to act with considerable delay only. Therefore, the stent is exposed to blood much longer so that vessel obliterations due to thrombosis occur more often, refer to F. Liestro, A. Colombo, "Late Acute Thrombosis after Paclitaxel Eluting Stent Implantation", Heart 2001, 86, 262-264. The healing time artificially prolonged in this manner constitutes a more or less open wound in the vessel wall which may easily lead to the formation of clots and thromboses. In this context thromboses were observed even one year after the successful and uncomplicated placement of stents finished with medical agents, cf. E. McFadden et al., Lancet 2004, 364, 1519-1521. Moreover, most recent findings and experience indicate that implants coated with proliferation-inhibiting medical agents appear to significantly increase the risk that patients may suffer heart attacks.

Also to be considered in this respect is that stents coated with medical agents tend to dispense the active agent in an irregular manner which impairs a controlled healing process after the stent has been placed.

Depending on the respective physiological conditions the release takes place phase-wise or in a delayed way. A delayed release detrimentally affects the desired purpose since especially in the days immediately following implantation a constant liberation of the active substance is a must. The phase-wise liberation is undesirable because the medical agents employed are most efficient systems causing damage if set free at higher than permissible concentrations.

From WO 2004/055153 A it is known to use aptamers for the coating of surfaces to promote the adhesion of biological material. The objects so coated may be implants and among them those intended for the vascular system. The biological material in this context may, for example, be stem cells, epithelial cells and the like as well as precursor cells. The aptamers are bound to the surface of the implant. The surface, i.e. the implant, may consist of plastic material. The attachment takes place in a photochemical manner.

Plastic coatings are difficult to apply in particular to stents because significant stresses will act on the coating due to the stent being crimp-mounted on a customary implantation balloon and expansion taking place subsequently. Therefore, a great number of plastic materials are unsuited for such coating purposes. Acrylate materials are a good example here. Furthermore, the question whether plastic materials are suited as stent coatings for the vascular system has not been investigated sufficiently. Desirable for this purpose would be plastics materials suitable to promote the deposition of epithelial cells on the surface.

Another approach has been made using a phosphoryl choline coating for stents, refer to WO 01/01957 A. For this purpose phosphoryl choline, a cell membrane component of the erythrocytes, as part of a non-biodegradable polymer coat on the stent is used to produce a non-thrombogeneous surface. Depending on the molecular weight the active substance is absorbed by the coating or adheres to the surface.

Known moreover are special microproteins with up to 40 amino acids, with said microproteins being capable of assuming conformationally stable three-dimensional structures which renders them suitable for use as versatilely applicable binding molecules. Examples of such microproteins are cystine knot proteins (Krause et al., FEBS 2007, 274, 86-95).

SUMMARY

It is, therefore, the objective of the invention to provide implants, in particular stents, by means of which disadvantages associated with the known medical-agent based coatings are avoided and a reliable and controlled healing process is ensured, but in particular the settlement of epithelial cells on the surface is promoted.

DETAILED DESCRIPTION

This objective is reached by providing an implant, in particular a stent, of the kind first mentioned above which has an amino-functionalized parylene coat, an oligonucleotide and/or an oligopeptide, all featuring a specific bonding affinity towards CD34-positive cells.

As a rule, such affinity relates to human CD 34-positive cells.

The layer or coating within the scope of the invention is any kind of coating applied to the surface of the implant. Especially the amino-functionalized parylene coat, the oligonucleotides as well as the oligopeptides applied to the parylene coat or implant surface are to be seen as coatings within the meaning of the invention. Furthermore, modified surfaces such as oxide layers, hydroxylized, aminized or surfaces otherwise modified or layers of plastic or other materials are to be also regarded as coatings for the purpose of the invention. The implants according to the invention in any case are provided with an amino-functionalized parylene coating or an oligonucleotide coat or an oligopeptide coating, with combinations comprising the amino-functionalized parylene coating and oligonucleotide bonded to it being preferred.

Endothelial progenitor cells (EPCs) are CD34-positive cells. This means they interact and form a bond with oligonucleotides or aptamers that have a specific bonding capacity with respect to CD34-positive cells. It thus follows that coatings containing oligonucleotides in bonded form specifically reacting with CD34-positive cells are capable of extracting and bonding endothelial progenitor cells from the blood circulation system and secure them to the surface. These endothelial) cells are thus capable of producing an endothelial layer on the implant surface which promotes the ingrowth of the stent into the vessel wall.

In accordance with the invention oligonucleotides are primarily employed that have less than 100 bases and are customarily known by the term of aptamers. These are RNA- or DNA oligonucleotides showing a high affinity towards certain target structures. Such aptamers can be produced with a view to having a very high and specific bonding affinity with a multitude of targets. Such targets include for example amino acids, antibodies, proteins but also cells and in particular CD34-positive cells.

Processes that are intended to generate aptamers capable of detecting and most specifically bonding virtually any molecule on a molecular basis are known, for example the SELEX process. The same applies to the isolation of aptamers for selective protein bonding and inhibition of their functions.

In the same way, oligopeptides or "peptide aptamers" having the required affinity with CD34-positive cells may be employed as well. These peptides may be identified and produced by simple techniques known to persons skilled in the art.

Such oligopeptides are, for example, co-called cystine knot microproteins, peptidic biomolecules with 28 to 40 amino acids. They show a characteristic linkage of 6 cysteines to form one cystine knot and a three-stranded antiparallel folded beta sheet. Due to its high conformational stability microproteins can be functionalized by substituting individual or inserting additional amino acids within exposed loops which turns them into binding molecules suited for therapeutic applications.

Preferred are nucleotide aptamers or oligonucleotides.

For example, aptamers suitable for the purposes of the invention are the following nucleotide sequences which are known per:

ccg ccg tgc ggg gta att tct ttt cca taa cga t  (SEQ ID NO: 1)

tcc tgc agc ttc ctg atg ct  (SEQ ID NO: 2)

gat tgc ctg acg tca tag ag  (SEQ ID NO: 3)

cgg cgg ctg acg tca gag ccg  (SEQ ID NO: 4)

ccg tcg ttt tgt cgt ttt gtc.  (SEQ ID NO: 5)

Additional suitable nucleotide aptamers are those mentioned in WO 2004/055153 A which are expressly included here.

Moreover, the respective mirror-image aptamers may be employed as well.

Suitable oligonucleotides or aptamers in accordance with the invention are those which are capable of attaching to CD34-positive cells, as well as their chemically modified variants having an identical bonding behavior.

It is understood that the principle described here is not only suitable for stents but for any kind of implant which may benefit from an attachment to CD 34-positive cells, for example cardiac valves, closure elements for aneurysms or fistulas, vascular grafts, bone and joint substitutes, dental implants and the like. Implants within the scope of the invention are also temporary stents and dilatation balloons which are dealt with in the framework of inventions (temporary implants).

As coating for the inventive implants any type of amino-functionalized parylene coating may be employed that is capable of securing the oligonucleotides or aptamers used for the purpose of the invention. Especially suitable are those with parylene A and AM. Such coatings for example have a layer thickness in the range of 2 µm to 10 µm.

Investigations have shown that the surface of stents provided with an amino-functionalized parylene coating remains intact even after expansion has taken place, with epithelial progenitor cells readily depositing on such surfaces. The deposited cells show a natural morphology which is not the case with purely metallic stents. If the stent is coated with an amino-functionalized parylene the deposition of EPCs on the surface of the stent becomes significantly denser and is effected more quickly. In this manner the functionalized parylene coating to which an aptamer coating has been applied constitutes an implant surface most conducive to the quick settlement of EPCs.

Since the parylene coats are also capable of securing proteins from the blood stream an excellent basic coating system is achieved with high adhesive power for cells depositing on it in a relatively natural environment.

Coatings with parylene A and AM shall be named first in this context, but any other type of amino-functionalization may be used as well provided it is capable of bonding the aptamers to be used for this purpose in a covalent or other (adhesive) manner.

The implants are coated in a customary manner using the respective suitable materials, particularly making use of CVD low-pressure plasma processes.

Suitable as well are parylenes with amino functions which have been integrated by subsequent functionalization in a manner known per se. A function density ranging between $10^{10}$ and $10^{15}$, particularly between $10^{12}$ and $10^{14}$ of amino functions per cm$^2$, is regarded sufficient as a rule.

In essence the parylene coating of the inventive implants is to be viewed not only as being an adhesion promoter but also as an "active substance". Since oligonucleotides or aptamers attach to the metal surface of the stent in an inadequate manner only, anchoring groups are needed that are made available on a material which itself adheres well to the implant surface. This requirement is met with parylene coatings. The functionalized coating serves as carrier for the aptamers which in turn provide links for the EPCs, and, what is more, as a "docking site" for the EPCs.

The invention also provides for the oligonucleotides or aptamers to be bonded to another layer, for example a diamond-like-carbon (DLC) layer or another layer consisting of plastic material. DLC layers may, for example, be produced using the sputtering process in a vacuum chamber with graphite as substrate and the implant as target. In the event functionalizing is needed for bonding the oligonucleotides or aptamers this may be carried out in a manner known per se.

The implants according to the invention may additionally be provided with a haemocompatible layer, especially serving as a substrate or basic layer applied directly to the surface of the implant. In that case they are provided with one or more additional layers among which is at least one further layer to which the oligonucleotides or aptamers are bonded.

In particular, superficially applied oxide layers of the implant may also serve as haemocompatible layers, i.e. layers that, for example, may be produced through the superficial oxidation of a metal stent made of nitinol. The surfaces of an implant may also be modified by hydroxilation or amination in such a way that they are capable of binding oligonucleotides, oligopeptides or the aptamers thereof as provided for by the invention.

Therefore, the system's compatibility with blood is further improved through such a haemocompatible coating of, for example, a stent whereas the aptamers enable endothelial cells to quickly attach and thus ensure the stent may rapidly grow into the wall of the vessel. The uniform distribution of the oligonucleotides across the overall surface of the stent makes it possible that the cells, aside from endothelial cells also smooth muscle cells, can attach themselves in a uniform and controlled manner. Accordingly, cells are allowed to rapidly attach to the surface of the stent and at the clearances in the stent which counteracts restenosis and considerably diminishes the risk of thromboses developing, especially as the stent ingrowth time span is short. Investigations have shown that the 'docking' of the EPCs in fact only takes a few hours.

The haemocompatible layer may also be bonded in an adhesive or covalent manner to a polymer matrix, for example of polyacrylic acid, polyvinylpyrrolidone, polyethylene glycol or other polymers suitable for medical purposes. They or these may contain antithrombotic or antiproliferative active agents.

For the manufacture of implants provided with several coatings, the individual layers are applied in a customary way, for example using submersion or spraying techniques or processes.

It is understood that the implants in accordance with the invention may comprise several layers of haemocompatible materials and/or aminofunctionalized parylenes and/or aptamers.

The haemocompatible layer may also be applied to the stent as outer coat in the form of a biosoluble polymer so that this coat is dissolved or decomposed shortly after it has been introduced into the expanded vessel. Biosoluble polymers of this kind are known per se.

Finally, the invention relates to the use of aminofunctionalized parylene A as coating material for implants and, in particular, for vascular stents. Preferred are parylene A and AM with and without oligonucleotides, oligopeptides or aptamers bonded to them.

However, it shall be mentioned in this context that it is also possible to finish the inventive implants with molecularly imprinted polymers, i.e. with a layer that has a specific bonding affinity with CD 34-positive cells and contains molecularly imprinted polymers. These polymers may be provided in the form of a coating, but also in the form of nanoparticles to be solely or additionally applied to the surface of the implant.

Making use of the molecular imprinting technology synthetic materials for molecular identification may be produced that in terms of affinity are comparable with biological systems. Molecular imprinting is a template polymerization creating artificial molecular recognition sites. For this purpose the target molecules are mixed with functional monomers and crosslinking agents and subsequently subjected to a radicalic polymerization thus producing a highly crosslinked polymer. The target molecules in this case act as template with polymerization taking place around them. If the template molecules are eliminated by extraction hollow spaces are left in the polymer network, said hollow spaces being indicative of the spatial arrangement of functional groups. Freezing the structure in this way results in specific recognition sites being produced in the polymer material (C. Gruber-Traub et al., Polymer Preprints 2006, 47 (2), 901-902). The respective target structures of interest serve as target molecules, in the present case the target structures of the CD 34-positive cells or endothelial progenitor cells.

Implants within the scope of the invention are also temporary implants, for example temporary stents, which dissolve (magnesium stents) or are removed after a certain time of residence in the body. This also includes dilatation balloons. The functionality associated with these implants is based on an impregnation effect, i.e. the coating of the implant is transferred, for example, onto the vessel wall where it takes effect.

The invention claimed is:

1. A vascular implant comprising a coating, the coating being an aminofunctionalized parylene coating and an oligonucleotide having a specific bonding affinity with CD34-positive cells, the oligonucleotide having the sequence ccg ccg tgc ggg gta att tct ttt cca taa cga t (SEQ ID NO: 1).

2. The implant according to claim 1, wherein the CD 34-positive cells are endothelial cells.

3. The implant according to claim 2, wherein the CD 34-positive cells are endothelial progenitor cells.

4. The implant according to any one of claims 1 to 3, wherein the oligonucleotide chemically or physically bonded to the amino-parylene coat or to the implant surface.

5. The implant according to claim 1, wherein the amino-parylene coating is applied by means of a chemical vapor deposit (CVD) or plasma coating process.

6. The implant according to claim 1, wherein the amino-parylene coating is a parylene A or parylene AM coat.

7. The implant according to claim 6, wherein the parylene coating function density amounts to $10^{12}$ to $10^{14}$ amino functions per $cm^2$.

8. The implant according to claim 1, wherein the parylene coating additionally comprises a haemocompatible basic layer.

9. The implant according to claim 8, wherein the haemocompatible basic layer is an oxide layer, an implant surface obtained through amination, or a plastic layer.

10. The implant according to claim 8 or 9, wherein the implant contains the oligonucleotide bonded to the haemocompatible basic layer.

11. The implant according to claim 1, comprising a biosoluble outer coat.

12. The implant of claim 1, wherein the implant is a stent.

13. The implant of claim 12, wherein the stent is a coronary stent.

* * * * *

SEQUENCE LISTING

```
<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<223> OTHER INFORMATION: Sythetic Aptamer

<400> SEQUENCE: 1
ccgccgtgcg gggtaatttc ttttccataa cgat                              34

<210> SEQ ID NO 2
<211> LENGTH: 20
<212> TYPE: DNA
<213> ORGANISM: Artificial Sequence
<220> FEATURE:
<223> OTHER INFORMATION: Synthetic Aptamer

<400> SEQUENCE: 2
tcctgcagct tcctgatgct                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Aptamer

<400> SEQUENCE: 3
gattgcctga cgtcatagag                                              20

<210> SEQ ID NO 4
<211> LENGTH: 21
<212> TYPE: DNA
<213> ORGANISM: Artificial Sequence
<220> FEATURE:
<223> OTHER INFORMATION: Synthetic Aptamer

<400> SEQUENCE: 4
cggcggctga cgtcagagcc g                                            21

<210> SEQ ID NO 5
<211> LENGTH: 21
```

```
-continued
<212> TYPE: DNA
<213> ORGANISM: Artificial Sequence
<220> FEATURE:
<223> OTHER INFORMATION: Synthetic Aptamer

<400> SEQUENCE: 5
ccgtcgtttt gtcgttttgt c                                              21
```